United States Patent [19]

Freed et al.

[11] Patent Number: 5,169,379
[45] Date of Patent: Dec. 8, 1992

[54] IN-SERIES VENTRICULAR ASSIST SYSTEM AND METHOD OF CONTROLLING SAME

[75] Inventors: Paul S. Freed, Bloomfield Hills; Kevin P. Gage, Northville; Adrian Kantrowitz, Pontiac, all of Mich.

[73] Assignee: L-Vad Technology, Pontiac, Mich.

[21] Appl. No.: 365,817

[22] Filed: Jun. 14, 1989

[51] Int. Cl.5 ............................................ A61B 19/00
[52] U.S. Cl. ........................................ 600/18; 600/17
[58] Field of Search ............................. 128/672, 673; 600/16–18

[56] References Cited

U.S. PATENT DOCUMENTS

| | | | |
|---|---|---|---|
| 4,231,453 | 11/1980 | Kurtz et al. | 600/17 |
| 4,685,446 | 8/1987 | Choy | 600/18 |
| 4,692,148 | 9/1987 | Kantowitz et al. | 128/696 |
| 4,697,574 | 10/1987 | Karcher et al. | 600/18 |
| 4,733,652 | 3/1988 | Kantrowitz et al. | 128/672 |
| 4,794,910 | 1/1989 | Mushika | 600/18 |
| 4,796,606 | 1/1989 | Mushika | 600/18 |
| 4,809,681 | 3/1989 | Kantrowitz et al. | 128/708 |
| 4,832,005 | 5/1989 | Takamiya et al. | 600/18 |
| 4,902,272 | 2/1990 | Milder et al. | 600/16 |
| 4,931,036 | 6/1990 | Kanai et al. | 600/18 |

OTHER PUBLICATIONS

"Theoretical Considerations Regarding the Optimization of Cardiac Assistance by Intraaortic Balloon Pumping", IEEE Transactions on Biomedical Engineering vol. BME -30 #3 Mar. 1983; Jaron et al.
"On the Feasability of Closed-Loop Control of Intraaortic Balloon Pumping"; IEEE Transactions on Biomedical Eng. vol. BME-20 #6 Nov. 1973; Clark et al.
"Real-time Automation of Intra-aortic Balloon Pump", Progress in Artificial Organs, 1985, pp. 491–499, by Zelano et al.
"A Self-adjusting Intra-aortic Balloon Pump Controller," presented at the 29th ACEMB, Nov. 6–10, 1986, by Moskowitz et al.
Brochure entitled "The Datascope System 90," Copyright 1985, Datascope Corp.
Brochure entitled "K2000 Intra-aortic Balloon Pump," sold by Kontron Instruments, undated.
Brochure of Aries Medical, Inc. for the Aries Model 700 IABP control system, Copyright 1984.
Mansfield Scientific, Inc. brochure for the Series 300 intra-aortic balloon, pump, Copyright 1986.

*Primary Examiner*—William E. Kamm
*Assistant Examiner*—J. R. Jastrzab
*Attorney, Agent, or Firm*—Finnegan, Henderson, Farabow, Garrett & Dunner

[57] ABSTRACT

An in-series ventricular assist system for assisting the circulation of blood in a patient is disclosed. A pumping bladder is disposed in the thoracic aorta of the patient and selected physiologic events relating to each heart beat are monitored by appropriate sensors. A gas handling subsystem inflates and deflates the pumping bladder in accordance with the detected physiologic events and a predetermined set of assist system parameters. A microprocessor evaluates the effects of inflation and deflation of the pumping bladder and the corresponding assistance on the patient for each heart beat. The microprocessor is operable to alter or adjust the assist system parameters for each subsequent heart beat in accordance with the effects of assistance of the pumping bladder on the patient. In the preferred embodiment, the assist system parameters which are set by the microprocessor for inflating and deflating the pumping bladder during the immediately preceding heart beat are used as the base line for making small adjustments in those parameters for the present heart beat. Alternatively, the microprocessor may be made operable to store the assist system parameters associated within an immediately preceding predetermined number of prior heart beats to compare the detected physiologic events from each of the stored preceding heart beats with those of the current heart beat.

21 Claims, 8 Drawing Sheets

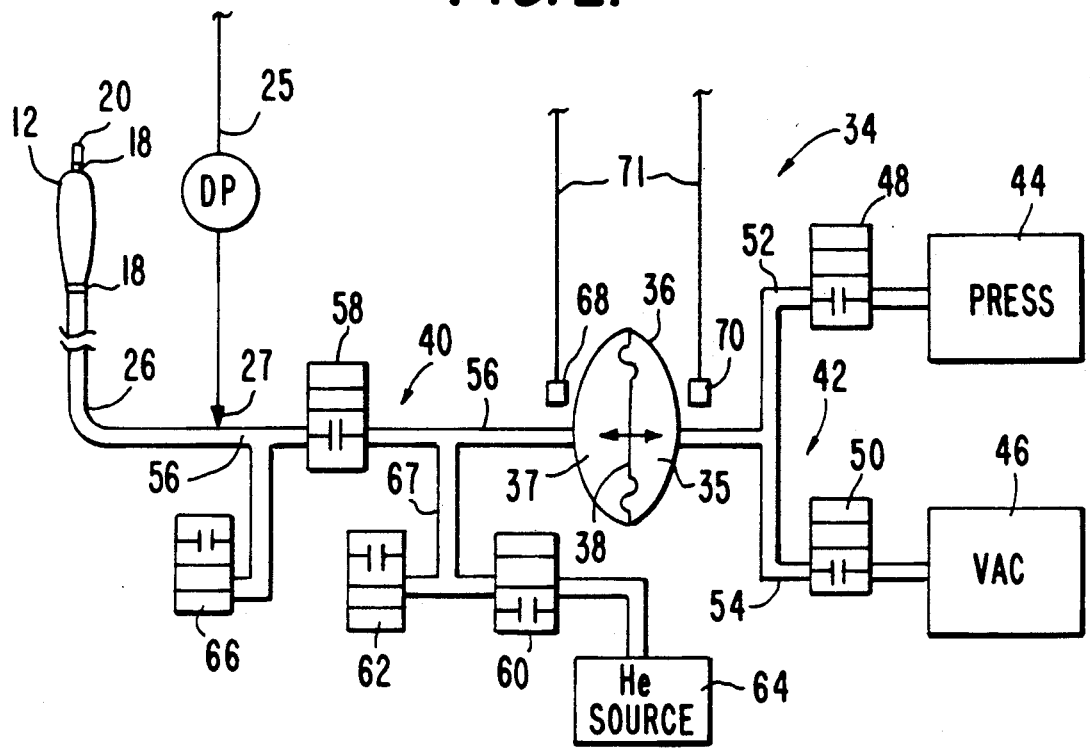

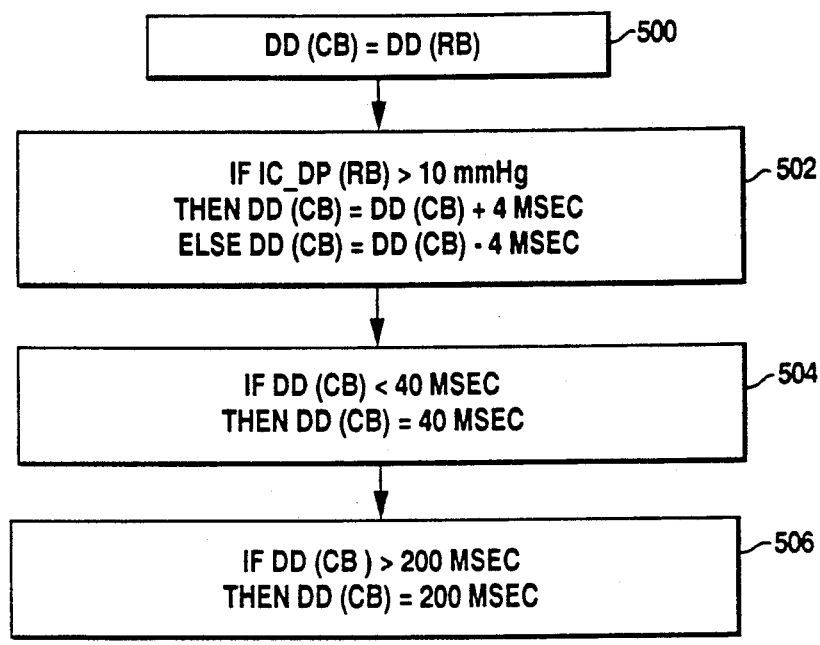
FIG. 9 DEFLATION DURATION SUB-ROUTINE
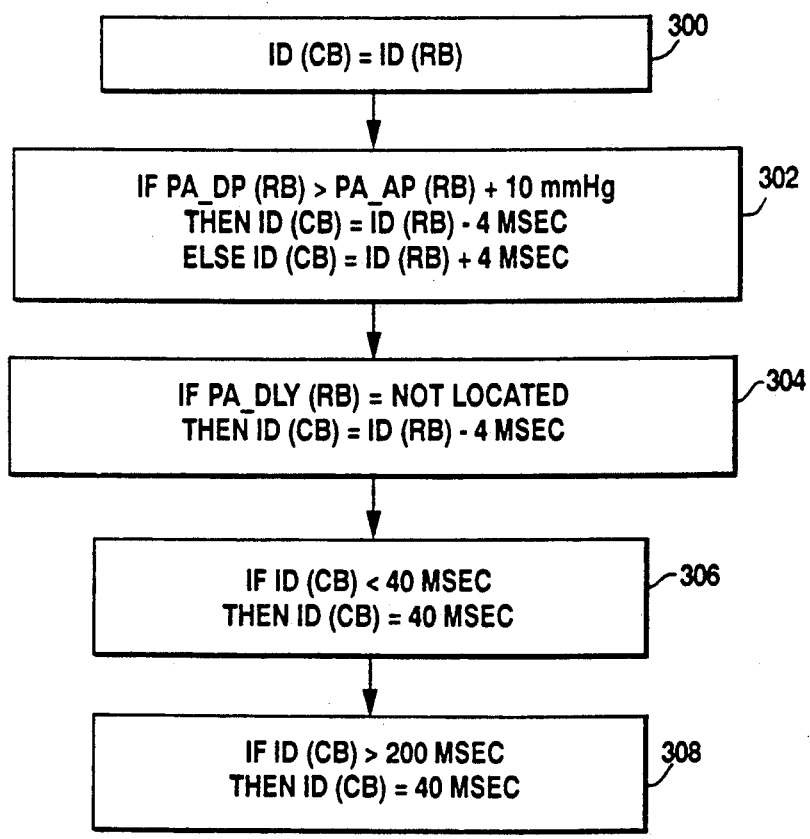
FIG. 11 INFLATION DURATION SUB-ROUTINE

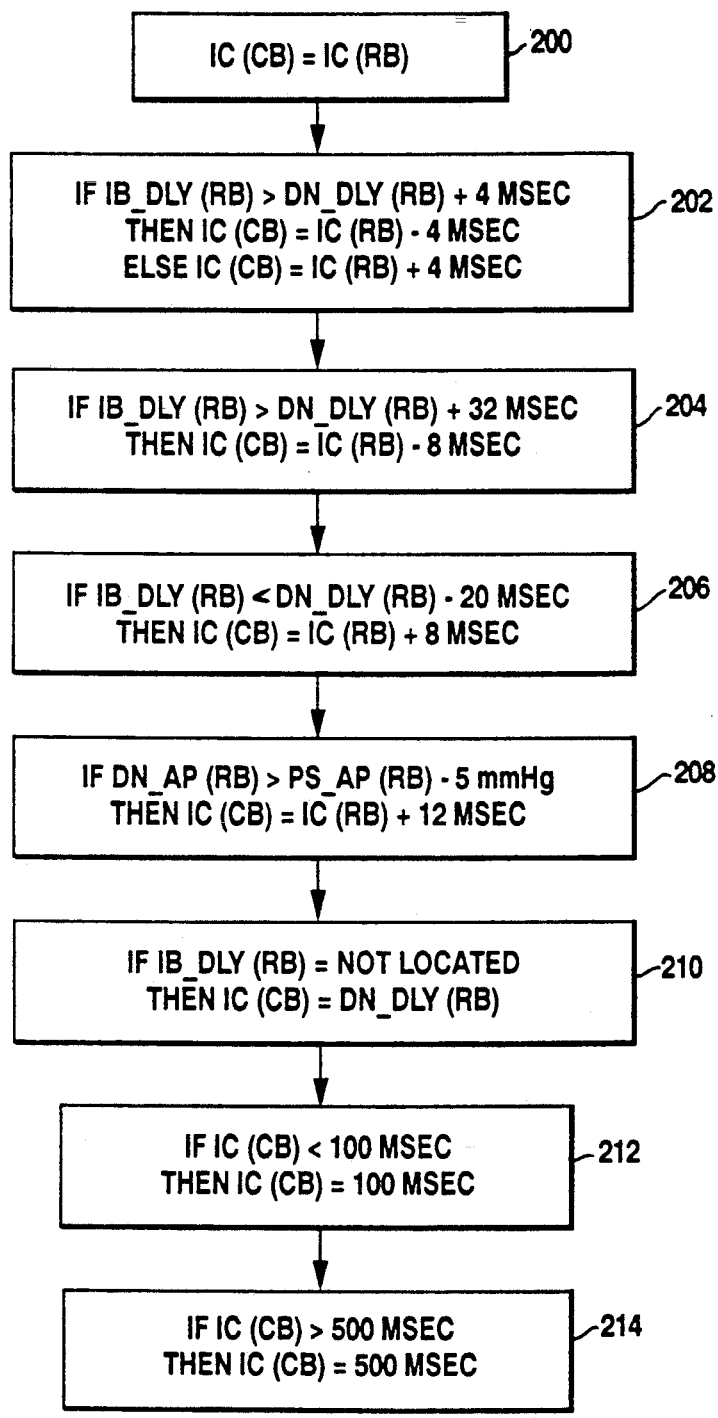

IN-SERIES VENTRICULAR ASSIST SYSTEM AND METHOD OF CONTROLLING SAME

BACKGROUND OF THE INVENTION

1. Field of the Invention

The present invention relates generally to ventricular assist devices, and particularly to a system and method for powering and controlling a pneumatic, in-series left ventricular assist device used to assist patients experiencing heart failure.

2. Description of the Related Art

Pneumatic, in-series left ventricular assist devices can be grouped into two classes according to their intended duration of use: temporary, in use for a few hours to a few weeks; and permanent, in use for the remaining life of the patient.

The temporary version is more commonly known as an intraaortic balloon pump (IABP). It has been in widespread clinical use since about 1967. The permanent version has undergone extensive experimental and limited clinical use. It is referred to alternatively as a mechanical auxiliary ventricle (MAV) or a dynamic aortic patch.

Both classes of assist device involve the placement of an avalvular pumping bladder into the descending thoracic aorta of the patient. To accomplish its pumping function, the pumping bladder is cyclically inflated synchronously with the natural heart beat. Inflation of the pumping bladder, with a shuttle gas such as helium, is timed to occur immediately after the aortic valve has closed. The volume of blood displaced as the pumping bladder is inflated causes an increase in diastolic blood pressure and, consequently, an increase in coronary artery blood flow. This increased blood flow increases the oxygen supply available to nourish the heart muscle. Later in the heart cycle, just prior to the opening of the aortic valve, the shuttle gas is exhausted from the pumping bladder causing a drop in systolic blood pressure which leads to a decrease in the oxygen requirement or demand of the heart and an increase in the amount of blood pumped. Thus, in-series left ventricular assistance increases mean blood pressure, increases blood flow, (i.e., cardiac output) and improves the oxygen supply/demand ratio in the heart.

The magnitude of these beneficial changes, and therefore the amount of hemodynamic assistance the patient receives, depends on the displacement volume of the pumping bladder and the accuracy with which the timing of the inflation/deflation cycle matches the opening and closing of the aortic valve. With regard to the first, maximum pumping bladder displacement is limited by anatomical considerations. With regard to the second, accuracy of timing in a conventional IABP system is sought in the following manner. The patient's ECG is monitored to detect occurrence of the QRS wave and it is assumed that the opening of the aortic valve follows the occurrence of the QRS wave by a fixed time interval. The closing at the aortic valve is assumed to follow by a somewhat longer, fixed time interval. These time intervals are estimated by an operator while looking at the displayed aortic pressure. The controller monitoring the electrocardiogram detects the occurrence of each QRS wave and uses the operator estimated time intervals to control the inflation and deflation of the pumping bladder.

The newest, commercially available IABP systems make one small improvement in the system described above. These systems assume that the time delays between the QRS wave and the opening and closing of the aortic valve are a function of the heart rate. A family of function curves relating heart rate to time delays from occurrence of the QRS wave to opening and closing of the aortic valve has been determined statistically from a large number of patients. However, in these newest systems the operator is still required to estimate the time intervals between the QRS wave and opening and closing of the aortic valve at the patient's present heart rate. The system then selects a specific member of the family of function curves based on the operator estimates of the noted time intervals.

Such statistically based information is, however, correct only on the average. For any specific patient the estimates are usually wrong. Furthermore, even for one specific patient at one specific heart rate the time intervals vary depending on the patient's present hemodynamic condition. Patients in whom an intraaortic balloon pump is placed are usually hemodynamically unstable. Thus, adjustment of timing of inflation and deflation of the pumping bladder may be necessary even if the patient's heart rate remains constant.

Therefore, contrary to labels otherwise, timing of inflation and deflation in prior art IABP and MAV systems is manual, and the responsibility of the operator. Arrhythmia, essentially random variation of instantaneous heart rate, makes accurate timing of inflation and deflation more difficult, even when a conscientious, well trained operator is present. The operator simply cannot react fast enough to adjust machine settings to each individual heart beat, thereby diminishing the effectiveness of the assist system.

It is therefore an object of the present invention to provide an automatic IABP system which converges on optimal timing adjustments for any heart rhythm, for any patient, without operator involvement.

It is another object of the present invention to provide an MAV system wherein a practical, long term solution for patients with heart failure is possible by enabling the system to work safely and effectively without operator supervision while the patient goes about his or her daily life at home, at work, at leisure, or in transit.

It is yet a further object of the present invention to provide an IABP system which is usable in localities where highly trained operators are unavailable.

It is yet another object of the present invention to expand the usefulness of IABP systems by maximizing their effectiveness under all possible conditions.

Additional objects and advantages of the invention will be set forth in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

To achieve the foregoing objects, and in accordance with the purposes of the invention as embodied and broadly described herein, an in-series left ventricular assist system for assisting the circulation of blood in a patient is provided, comprising: a pumping bladder for disposal in the thoracic aorta of a patient, and means for detecting selected physiologic events relating to each heart beat of the patient. A gas handling means is provided for inflating and deflating the pumping bladder in accordance with the detected physiologic events and a predetermined set of assist system parameters. Control means are provided for evaluating the effects of inflation and deflation of the pumping bladder and the corresponding assistance on the patient for each heart beat, and for altering the assist system parameters for each subsequent heart beat in accordance with the effects of assistance of the pumping bladder on the patient.

Preferably, the detecting means includes sensing means for sensing the electrocardiogram and the aortic blood pressure of the patient, and for generating signals in accordance with the measured electrocardiogram and aortic blood pressure.

In a preferred embodiment, the gas handling means comprises a shuttle gas circuit having a shuttle gas disposed therein, and means for pressurizing and depressurizing the shuttle gas in the circuit. The gas handling means further preferably includes means for adjusting the volume of shuttle gas delivered to the pumping bladder, and valve means for regulating the flow of shuttle gas to and from the pumping bladder.

It is still further preferable that the control means of the in-series left ventricular assist system incorporating the teachings of the present invention include a shuttle gas volume control means for maintaining a selected volume of shuttle gas in the shuttle gas circuit. The shuttle gas volume control means further includes means for monitoring a difference between pumping bladder pressure and the patient's aortic pressure when the pumping bladder is inflated, with the shuttle gas volume control means being operable to control the means for adjusting the volume of shuttle gas delivered to the pumping bladder in accordance with the monitored difference between pumping bladder pressure and the aortic pressure.

In a further embodiment of the present invention, the in-series left ventricular assist system includes means for storing the detected physiologic events and associated assist system parameters for a predetermined number of preceding heart beats prior to each subsequent heart beat, and means for comparing the detected physiologic events for each present heart beat with the stored physiologic events to select at least one of the predetermined number of preceding heart beats as a reference heart beat. The control means further includes means for evaluating the effects of inflation and deflation of the pumping bladder and the corresponding assistance on the patient for the selected preceding reference heart beat, and for altering the assist system parameters for each subsequent heart beat in accordance with the evaluated effects of assistance of the pumping bladder on the patient for the selected preceding reference heart beat.

In this further embodiment of the in-series left ventricular assist system of the present invention, the detecting means includes means for detecting each occurrence of a QRS wave and for measuring the time interval between successive QRS waves, and pressure sensing means for determining for each heart beat: a) a time interval between detection of the QRS wave and opening of the aortic valve; b) aortic pressure at opening of the aortic valve; c) a time interval between detection of the QRS wave and closing of the aortic valve; d) aortic pressure at closing of the aortic valve; e) a time interval between detection of the QRS wave and an initial effect on aortic pressure caused by inflation of the pumping bladder; and f) respective time intervals between detection of the QRS wave and the end of inflation and the end of deflation of the pumping bladder.

The present invention, as embodied and broadly described herein, further comprises a method for controlling inflation and deflation timing of an in-series left ventricular assist system, with the method including the steps of: detecting physiologic events relating to each heart beat; inflating and deflating the pumping bladder at selected times; storing, for a selected number of preceding heart beats, the detected physiologic events relating to the preceding heart beats and the selected times of inflation and deflation of the pumping bladder during the preceding heart beats; and adjusting the selected times of inflation and deflation of the pumping bladder for each subsequent heart beat in accordance with the effects of pumping bladder inflation and deflation on the stored physiologic events.

In a still further embodiment, the present invention provides a method for controlling, for each heart beat of a patient, the volume of inflation of an in-series left ventricular assist device, the assist device including a drive unit and pump means for cyclically inflating and deflating a pumping bladder disposed in the thoracic aorta of the patient, comprising the steps of: detecting selected physiologic events relating to each heart beat; detecting selected pneumatic events relating to each pump cycle within the drive unit; pumping shuttle gas into the pumping bladder for a selected inflation time interval; storing, for a selected number of preceding heart beats, the detected physiologic events, the detected pneumatic events, and the associated inflation time intervals; and adjusting the inflation time intervals for each subsequent heart beat according to a comparison of the stored detected physiologic events and the associated stored detected pneumatic events.

The method of the present invention for controlling the volume of inflation of an in-series left ventricular assist device may be modified to include the steps of adjusting the time interval of deflation of the pumping bladder for each subsequent heart beat according to a comparison of the stored detected physiologic events and the associated stored detected pneumatic events.

The basis upon which the system and method of the present invention operates will be broadly described below with specific embodiments described in the following section. Initially, for the first assisted heart beat, the system uses conservative default values for assist system parameters which may include, but are not limited to: time of inflation of the pumping bladder, time of deflation of the pumping bladder, duration of inflation of the pumping bladder, duration of deflation of the pumping bladder, and the volume of shuttle gas required for inflation of the pumping bladder. Then, after evaluating the effects of pumping bladder inflation on the hemodynamics of the patient, the value of each parameter is incremented or decremented a small amount to increase the effectiveness or assistance of the system on the patient. The adjusted assist system parameters are then used for the next heart beat. Up to twenty heart beats, with small changes in the parameters after each, may be required to converge on an "optimal" set of control or assist system parameters. Optimal, as used herein, means that all evaluations, which determine if an individual parameter needs adjustment, are either negative or cause stable oscillation. The steps of evaluating and making small adjustments are repeated on every heart beat indefinitely. Thus, the system tracks any changes in the physiologic condition of the patient. The system and method of the present invention wherein multiple cumulative small adjustments are made, rather than calculating and implementing the change in a single step, allows safe and effective utilization of the system to proceed even in the presence of noise in monitored signals and occasional errors in detecting the pertinent physiologic events.

The description of the preceding paragraph assumes that most heart beats are very similar to the immediately prior heart beat and, thus, corrections or adjustments to the assist system parameters for a present heart beat may be made utilizing the known assist system parameter values of the immediately preceding heart beat. However, when there is beat to beat variation in ventricular events, a common situation for patients needing ventricular assistance, an additional level of control is required. Instead of adjusting the assist system parameters in accordance with the parameters associated with the immediately preceding beat, a reference heart beat, selected from a predetermined number of prior heart beats, for instance those occuring in the latest one minute interval, which more closely approximates the present beat, is used.

To implement this strategy, the values of all assist system parameters and appropriate descriptors of the patient's hemodynamic state for the predetermined number of immediately preceding or prior heart beats are stored in a memory. On the detection of each new heart beat, the respective physiologic parameters are compared with those of the prior heart beats stored in memory, and a reference heart beat is selected. The assist system parameters associated with the reference heart beat are then adjusted to determine the appropriate assist system parameters for the present heart beat.

BRIEF DESCRIPTION OF THE DRAWINGS

The accompanying drawings, which are incorporated in and constitute a part of the specification, illustrate presently preferred embodiments and methods of the invention and, together with the general description given above and the detailed description of the preferred embodiments and method given below, serve to explain the principles of the invention.

FIG. 2 schematically illustrates components of a preferred embodiment of the gas handling subsystem of FIG. 1;

FIG. 3 illustrates the cyclic operation and corresponding states of the valves of the gas handling subsystem of FIG. 2;

FIG. 9 is a flowchart illustrating the rules for the Deflation Duration Adjustment Sub-routine of the main processing loop;

FIG. 10 is a flowchart illustrating the steps or rules for the Inflation Command Adjustment Sub-routine of the main processing loop;

FIG. 11 is a flowchart illustrating the steps or rules for the Inflation Duration Adjustment Sub-routine of the main processing loop.

DESCRIPTION OF THE PREFERRED EMBODIMENTS

Figure 1:
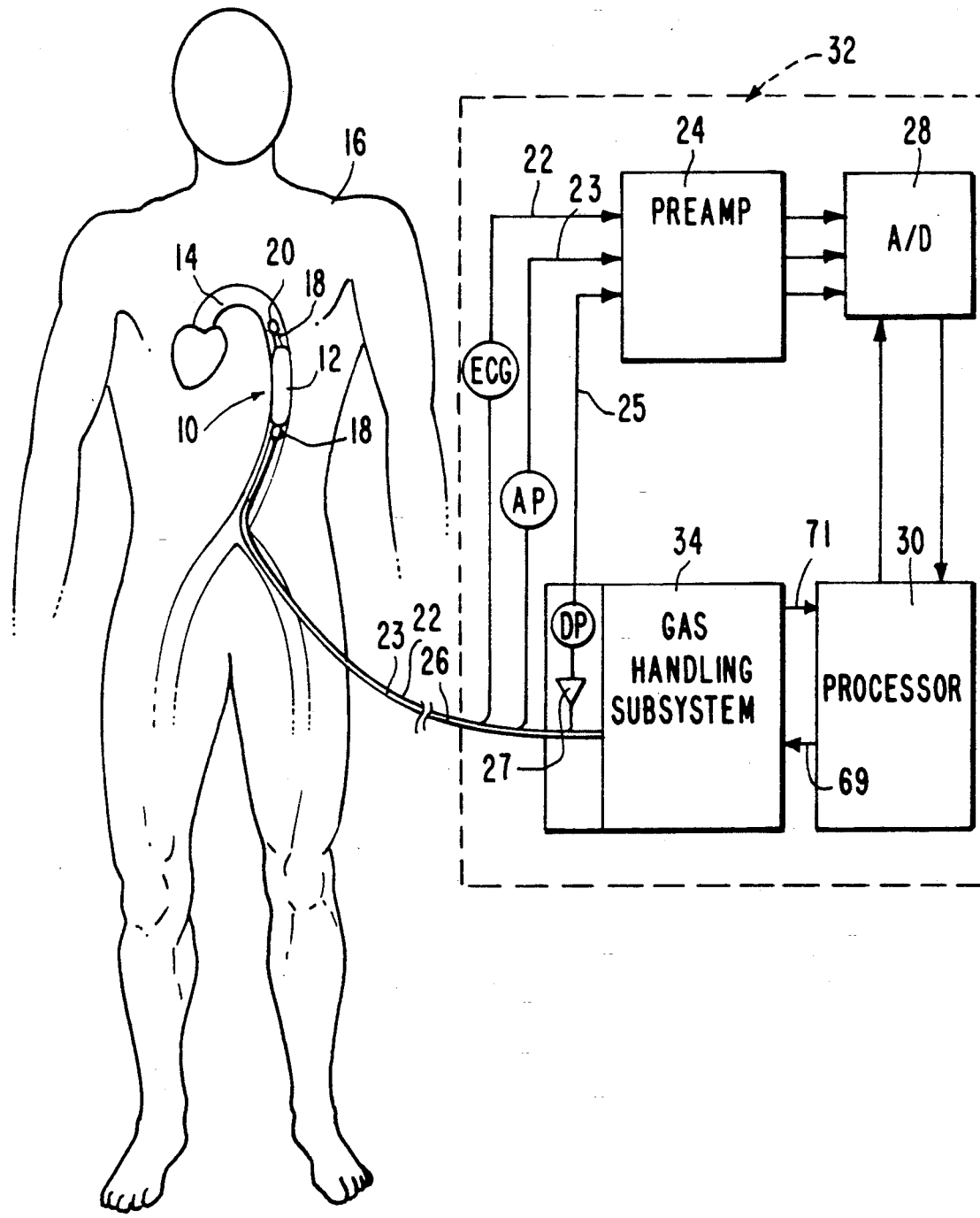
FIG. 1 illustrates the components of an intra-aortic balloon pump system incorporating the teachings of the present invention.

Reference will now be made in detail to the presently preferred embodiments of the invention as illustrated in the accompanying drawings, in which like reference characters designate like or corresponding parts throughout the several drawings.

The method and apparatus of the present invention will now be described as it is implemented for an IABP. The use of the present invention for controlling an MAV is analogous to the following description for an IABP.

FIG. 1 illustrates an in-series left ventricular assist system comprising an intra-aortic balloon pump generally referred to as 10, having a pumping bladder 12 disposed in a thoracic aorta 14 of a patient 16.

In accordance with the present invention there is provided means for detecting selected physiologic events relating to each heart beat of the patient. Preferably, the detecting means includes sensing means for sensing the electrocardiogram and the aortic blood pressure of the patient, and for generating signals in accordance with the sensed electrocardiogram and aortic blood pressure. As embodied herein, the sensing means includes electrodes 18 disposed on both sides of pumping bladder 12 for sensing the electrocardiogram (ECG) of the patient, and a pressure sensor 20 disposed at the end of pumping bladder 12 near the patient's heart for measuring the aortic pressure (AP) of the patient. The sensing means further includes leads 22 extending between each electrode 18 and a preamplifier 24, and leads 23 extending between pressure sensor 20 and preamplifier 24. Leads 22 and 23 may be incorporated in a catheter 26 extending from pumping bladder 12 as is conventional in an intra-aortic balloon pump.

Signals generated by electrodes 18 and pressure sensor 20 are preferably routed through preamplifier 24 across leads 22 and 23 and from preamplifier 24 to an analog to digital converter 28. Analog to digital converter 28 acts to digitize the analog signals from electrodes 18 and pressure sensor 20. Digitized representations of the signals corresponding to the ECG and the AP are then fed to a processor 30. The function and operation of processor 30 will be described in more detail hereinafter. If desired, preamplifier 24, analog to digital converter 28, and processor 30 may be incorporated in a bedside drive console graphically depicted in FIG. 1 by reference numeral 32.

In accordance with the present invention the in-series left ventricular assist system further includes gas handling means for inflating and deflating the pumping bladder in accordance with the detected physiologic events and a predetermined set of assist system parameters. As embodied herein, the gas handling means includes a gas handling subsystem generally referred to as 34 which may be conveniently incorporated in bedside drive console 32. Signals are passed between processor 30 and gas handling subsystem 34 as schematically illustrated with lead lines 69. With reference to FIG. 2, a first embodiment of gas handling subsystem 34 comprises an isolation chamber 36, divided into an air side compartment 35 and a shuttle gas side compartment 37 by a movable diaphragm 38. A shuttle gas circuit generally referred to as 40 is connected to compartment 37 of isolation chamber 36, and an air circuit generally referred to as 42 is connected to compartment 35 of isolation chamber 36.

Gas handling subsystem 34 further includes means for pressurizing and depressurizing a shuttle gas disposed in the shuttle gas circuit. As embodied herein, the pressurizing and depressurizing means includes a source of regulated compressed air 44, a source of regulated vacuum 46 and control valve means comprised of control valves 48 and 50 disposed in respective air conduits 52 and 54 connecting the source of pressurized air 44 and vacuum 46, respectively, to air circuit compartment 35 of isolation chamber 36. Shuttle gas circuit 40 includes a conduit 56 connected to catheter 26 leading in turn to pumping bladder 12. Pumping bladder 12 may be cyclically inflated and deflated by pressurizing and depressurizing the shuttle gas disposed in shuttle gas circuit 40. In the preferred embodiment, the shuttle gas is pressurized or depressurized by movement of diaphragm 38 within isolation chamber 36. Diaphragm 38 is displaced to the left in FIG. 2 by opening control valve 48 to allow passage of pressurized air through conduit 52 into air side compartment 35 of isolation chamber 36. The isolation chamber is depressurized by opening of control valve 50 to thereby connect regulated vacuum 46 to air side compartment 35 of isolation chamber 36 thus moving diaphragm 38 to the right in FIG. 2 and drawing shuttle gas into the shuttle gas side compartment 37 of isolation chamber 36. Preferably, control valves 48 and 50 comprise solenoid valves operable between open and closed positions by signals generated by processor 30 as is conventional in control valves.

With continued reference to FIG. 2, the preferred shuttle gas in shuttle gas circuit 40 is helium since it flows through small diameter tubes faster than air. Shuttle gas circuit 40 further includes a common valve 58 disposed in conduit 56 between pumping bladder 12 and shuttle gas side compartment 37. Common valve 58 is operable between an open and closed position to connect or isolate shuttle gas side 37 of isolation chamber 36 from pumping bladder 12. The time available from when pumping bladder 12 needs to be deflated to when it needs to be inflated is usually longer than the time required to empty all shuttle gas from pumping bladder 12. If common valve 58 is closed after all gas is removed from pumping bladder 12, then the pressurization of isolation chamber 36 can begin even while the pumping bladder 12 is evacuated. This "precharging" of the isolation chamber allows faster inflation of the pumping bladder when the common valve 58 is reopened.

Similarly, the time available from when pumping bladder 12 needs to be inflated to when it needs to be deflated is usually longer than the time required to fill the pumping bladder with shuttle gas. If common valve 58 is closed after the pumping bladder is completely filled, then depressurization of the isolation chamber can begin even while pumping bladder 12 is inflated. This "precharging" of the isolation chamber allows faster deflation of the pumping bladder. This "precharging" function is not limitive of the scope of the present invention since it is possible, in at least one embodiment of the system of the present invention, to perform all of the described functions of common valve 58 by appropriately sensitive manipulation of control valves 48 and 50 to time the inflation and deflation of the pumping bladder, thus eliminating common valve 58. Moreover, and as described in more detail later, control valves 48 and 50 may be replaced with a reciprocating piston type drive for pressurizing and depressurizing the shuttle gas circuit.

Shuttle gas circuit 40 further includes a helium fill valve 60, a helium exhaust valve 62, and a source of helium 64 disposed in a leg 67 of shuttle gas circuit 40. Helium fill valve 60 and helium exhaust valve 62, operated in conjunction with the source of helium 64, comprise a means for maintaining a selected volume of shuttle gas in shuttle gas circuit 40.

In one embodiment of the system incorporating the teachings of the present invention, the means for maintaining a selected volume of shuttle gas in shuttle gas circuit 40 includes means for monitoring a difference beween the inflated pressure of pumping bladder 12 and the patient's aortic pressure.

By way of example and not limitation, the monitoring means may include a pressure sensor 27 disposed in catheter 26 near pumping bladder 12. Alternatively, pressure sensor 27 may be disposed in conduit 56. Pressure sensor 27 may then be operably connected to processor 30 via lead line 25 to provide a signal corresponding to the drive pressure (DP) of the shuttle gas in pumping bladder 12 or conduit 56. Processor 30 then compares the pressure of shuttle gas in pumping bladder 12, or conduit 56, to the patient's aortic pressure (AP) as monitored by pressure sensor 20 to determine a difference therebetween. If that difference falls above or below predetermined threshold levels, processor 30 generates signals to operate a respective one of the helium fill valve 60 or helium exhaust valve 62 to add or exhaust shuttle gas to shuttle gas circuit 40. The threshold levels of the pressure difference are preferably selected to insure complete inflation of pumping bladder 12 without causing over-inflation.

Alternatively, processor 30 may be configured to maintain the pressure of pumping bladder 12 within threshold levels by appropriately controlling the period of time common valve 58 remains open during inflation to increase or decrease the volume of shuttle gas delivered to pumping bladder 12 while maintianing a constant volume of shuttle gas in shuttle gas circuit 40.

Shuttle gas circuit 40 may further include a safety valve 66 which deflates pumping bladder 12 if electrical power to the system is lost or if processor 30 detects some failure condition.

In accordance with the present invention, gas handling subsystem 34 further includes means for detecting displacement of the diaphragm within the isolation chamber. As embodied herein, the means for detecting displacement of diaphragm 38 includes a pair of proximity sensors 68 and 70 disposed in the walls of isolation chamber 36 on opposite sides of diaphragm 38. Proximity sensors 68 and 70 detect when diaphragm 38 reaches either wall of isolation chamber 36 thereby indicating full displacement of diaphragm 38 in either the pressurization or depressurization state. The proximity sensors generate signals when contacted by diaphragm 38, which signals are passed to processor 30 over lines 71. Alternatively, proximity sensors 68 and 70 may be replaced by a continuous position sensor which senses the position of diaphragm 38 in isolation chamber 36.

Figure 4:
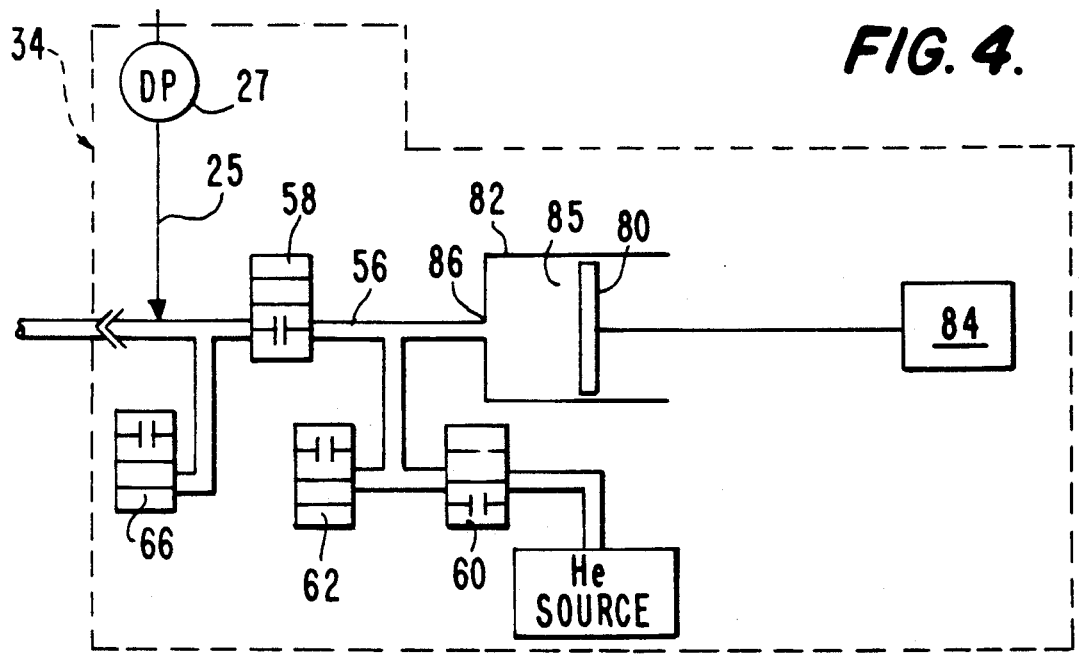
FIG. 4 schematically illustrates a second embodiment of the gas handling subsystem of the present invention.

With reference to FIG. 4, a second embodiment of gas handling subsystem 34 may be used wherein the isolation chamber, the source of compressed air, the regulated vacuum, and control valves 48 and 50 may be replaced with a reciprocating piston 80 disposed in a cylinder 82. Piston 80 may be powered by a drive means 84 which might comprise, for example, a solenoid, a motor lead screw combination, or any other conventional means for reciprocating piston 80 in cylinder 82. The drive means is operably connected to processor 30 by conventional means to control the movement of piston 80. An outlet 86 from a chamber 85 defined by piston 80 and cylinder 82 is connected directly to conduit 56 to pressurize and depressurize the shuttle gas as piston 80 reciprocates in cylinder 82.

Moreover, with appropriate control of piston 80 in the second embodiment of gas handling subsystem 34, or with appropriate control of control valves 48 and 50 in the first embodiment of subsystem 34 illustrated in FIG. 2, common valve 58 may be eliminated while still accomplishing the functions of the gas handling subsystem.

In accordance with the present invention, the in-series left ventricular assist system further includes control means for evaluating the effects of inflation and deflation of the pumping bladder and the corresponding assistance on the patient for each heart beat, and for altering the assist system parameters for each subsequent heart beat in accordance with the effects of assistance of the pumping bladder on the patient. With reference to FIG. 1 and as embodied herein, the control means comprises processor 30. Processor 30 may comprise a microprocessor or minicomputer which receives and processes signals from analog to digital converter 28 to thereby control the times of initiation and the duration of inflation and deflation cycles of pumping bladder 12. In the preferred embodiment described herein, processor 30 is operably connected to control valves 48 and 50; common valve 58; helium fill valve 60; helium exhaust valve 62; and safety valve 66 by an appropriate number of cables graphically represented by lead lines 69 illustrated in FIG. 1. Each of these valves is movable between an open and closed position in accordance with signals generated by processor 30. The times of initiation of opening and closing of selected ones of those valves, and the duration of the open and closed states are determined based on a specific set of assist system parameters which are continually adjusted by processor 30 to optimize the effects of assistance of the pumping bladder on the patient. Prior to discussing and describing one possible set of assist system parameters, and to assist in the understanding of the nature of the present invention, the various "states" of the gas handling subsystem will be described with reference to FIG. 3, which illustrates the cyclic opening and closing of each of the control valves listed above.

PURGE AND FILL CYCLE

When the system of the present invention is initialized to begin ventricular assistance, processor 30 initiates an automatic purge and fill cycle which precedes initiation of inflation of pumping bladder 12. Initially, all valves except safety valve 66 are placed in the closed position. This ensures that the pumping bladder 12 is deflated when not in use so as to not interfere with normal blood circulation within the patient. State 1 as illustrated in FIG. 3 shows this condition.

Next, as illustrated in state 2 of FIG. 3, control valve 48 and helium exhaust valve 62 are opened to pressurize air side 35 of isolation chamber 36 with pressurized air from source 44 to thereby displace diaphragm 38 towards the shuttle gas circuit side of isolation chamber 36 and to exhaust, through helium exhaust valve 62, the gas within shuttle gas side 37 of isolation chamber 36.

Next, as illustrated in state 3, safety valve 66 is closed and is held closed until the assist system is shut down or until a failure is detected. At the same time, common valve 58, helium fill valve 60 and control valve 50 are opened; and helium exhaust valve 62 and control valve 48 are closed to fill shuttle gas side 37 of isolation chamber 36 with pure shuttle gas. This state is maintained until the pressure of shuttle gas in conduit 56 exceeds a threshold value which, by way of example and not limitation, may be set at 5 mm Hg as measured by pressure sensor 27.

In state 4, the valves are operated to the respective positions illustrated for a predetermined period of time to exhaust the air helium mixture from shuttle gas circuit 40. Then, the valves are operated to the positions illustrated in state 5 of FIG. 3 to refill shuttle gas circuit 40 with helium until the drive line pressure in conduit 56 exceeds a predetermined negative pressure which, by way of example and not limitation, may be set at −40 mm Hg. The pressure at which filling is terminated determines the amount of shuttle gas in shuttle gas circuit 40. In state 6, air side 35 of isolation chamber 36 is pressurized from source of compressed air 44 until the signal is given to inflate pumping bladder 12 by opening common valve 58.

States 1 through 5 and the respective opened and closed positions of the valves completes the "purge and fill" cycle, which cycle is repeated every time the system is restarted. Preferably, during operation, the "purge and fill" cycle is repeated on a nominal two hour basis in order to exhaust moisture which may have entered the pumping bladder.

Figure 12:
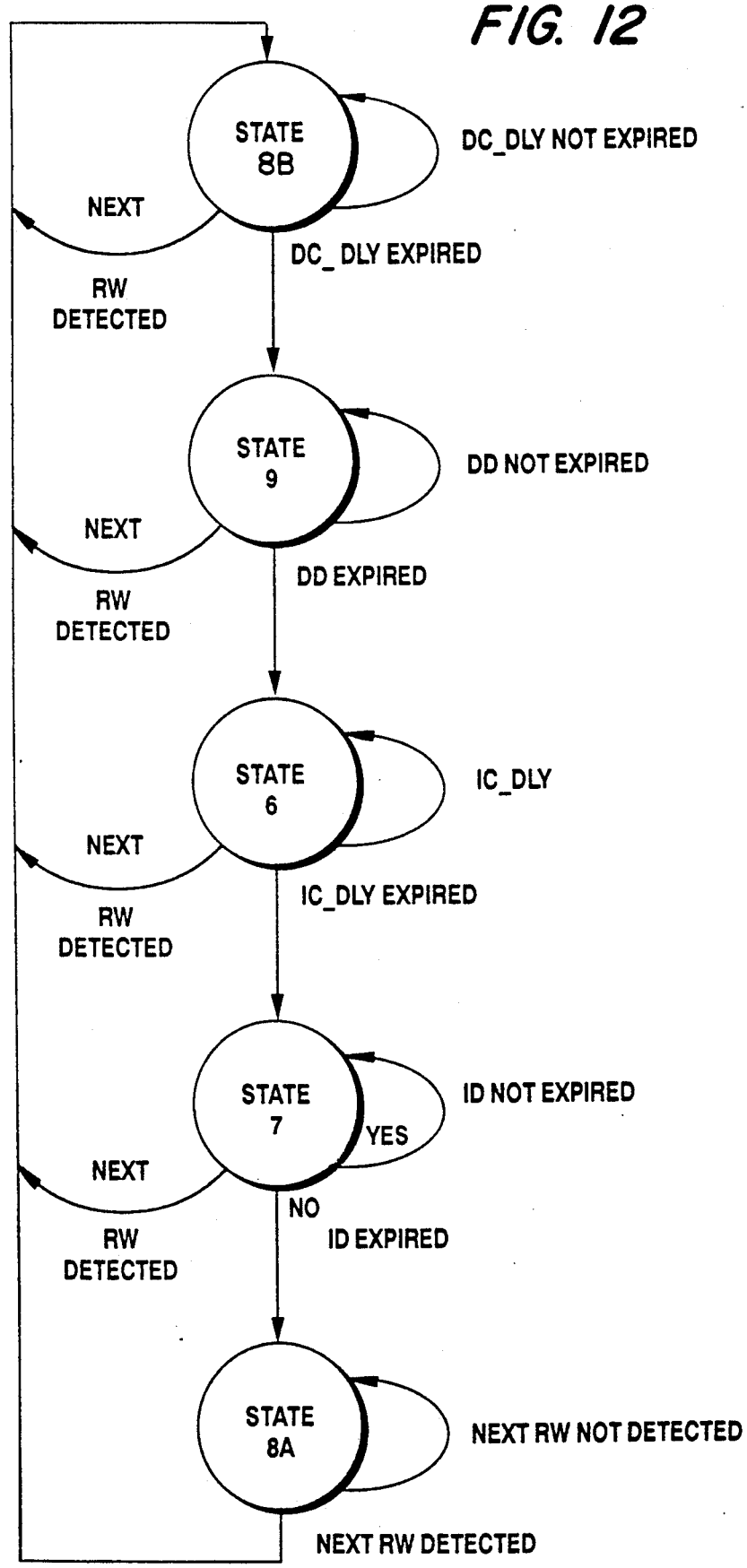
FIG. 12 is a flowchart illustrating the logic of the control means of the preferred embodiment of the present invention to cycle the states of the valves of the gas handling means during ventricular assistance.

The remaining states 6–9 illustrated in FIGS. 3 and 12 represent the cyclic operation of pumping bladder 12 during operation of the system of the present invention as will be described in detail below.

As discussed above, signals from the electrode 18 which represent the electrocardiogram of a patient, and signals from pressure sensor 20 which detect the aortic pressure of the patient, are transmitted through preamplifier 24 and analog to digital converter 28 to processor 30. In accordance with the present invention processor 30, comprising the control means, is operable to detect, in accordance with the measured ECG, the respective times of occurrence of each QRS wave, and is further operable to measure the time interval between successive QRS waves.

Processor 30 is further operable to determine the aortic pressure at opening of the aortic valve of the patient and the aortic pressure at closing of the aortic valve from the signals generated by pressure sensor 20. Utilizing the signals from electrodes 18 and pressure sensor 20, processor 30 determines the following for each heart beat: a) a time interval between detection of the QRS wave and opening of the aortic valve; b) aortic pressure at opening of the aortic valve; c) a time interval between detection of the QRS wave and closing of the aortic valve; d) aortic pressure at closing of the aortic valve; e) a time interval between detection of the QRS wave and an initial effect on aortic pressure caused by inflation of the pumping bladder; and f) respective time intervals between detection of the QRS wave and the end of inflation and the end of deflation of the pumping bladder.

In accordance with the present invention the control means, in the preferred embodiment comprised of processor 30, initiates inflation of the pumping bladder at a predetermined time delay after detection of the QRS wave. The predetermined time delay for initiating inflation of the pumping bladder is selected by processor 30 in accordance with the time interval between the closing of the aortic valve and initial effect of pumping bladder inflation on aortic pressure for the selected preceding heart beat. Processor 30 also selectively adjusts a predetermined period of time of inflation of the pumping bladder for each heart beat such that the amount of shuttle gas admitted into the pumping bladder is sufficient for complete inflation of the pumping bladder while maintaining a transmembrane pressure of less than a predetermined amount. By way of example and not limitation, the predetermined transmembrane pressure of the pumping bladder is maintained at less than about 50 mm Hg.

Similarly, the control means, comprised of processor 30 in the preferred embodiment, initiates deflation of the pumping bladder at a predetermined time delay after detection of the QRS wave, with the predetermined time delay for initiating deflation being selected by processor 30 in accordance with: a) the temporal relationship between the detected opening of the aortic valve, the end of pumping bladder deflation, and the detected closing of the aortic valve; and b) the aortic pressure at the opening of the aortic valve and the aortic pressure at the closing of the aortic valve. Processor 30 also selectively adjusts a predetermined period of time of deflation of the pumping bladder for each heart beat such that the amount of shuttle gas removed from the pumping bladder is sufficient to empty the pumping bladder while maintaining residual intraballoon pressure to no less 10 mm Hg.

As discussed above, the control means of the system of the present invention comprised of processor 30, also comprises means for determining, for each hear-t beat: the initiation of deflation of the pumping bladder, the duration of deflation of the pumping bladder, the initiation of inflation of the pumping bladder, and the duration of inflation of the pumping bladder. In order to optimize the effects of assistance of the cyclic inflation and deflation of the pumping bladder on the patient these times of initiation and durations of inflation and deflation are adjusted for each heart beat based on prior values associated with a preceding heart beat. The selected preceding heart beat may be the heart beat immediately preceding the present heart beat. Alternatively, the selected preceding heart beat may be one for which the associated physiologic events most closely match the associated physiologic events of the present heart beat. To achieve this function and in accordance with the present invention, the assist system includes means for storing the detected physiologic events and associated assist system parameters for a predetermined number preceding heart beats prior to each subsequent heart beat; and means for comparing the detected physiologic events heart beat with the stored physiologic events to select at least one of the predetermined number of preceding heart beats as a reference heart beat. Thereafter, the associated times and durations of inflation and deflation of the pumping bladder for the referenced heart beat are adjusted for present heart beat in accordance with a predetermined set of rules which have been determined to optimize the assistance of inflation and deflation of the pumping bladder on the patient. As embodied herein, processor 30 comprises the means for storing the detected physiologic events and associated assist system parameters, and also comprises the means for comparing the detected physiologic events with the stored physiologic events.

MAIN PROCESSING LOOP

Figure 7:
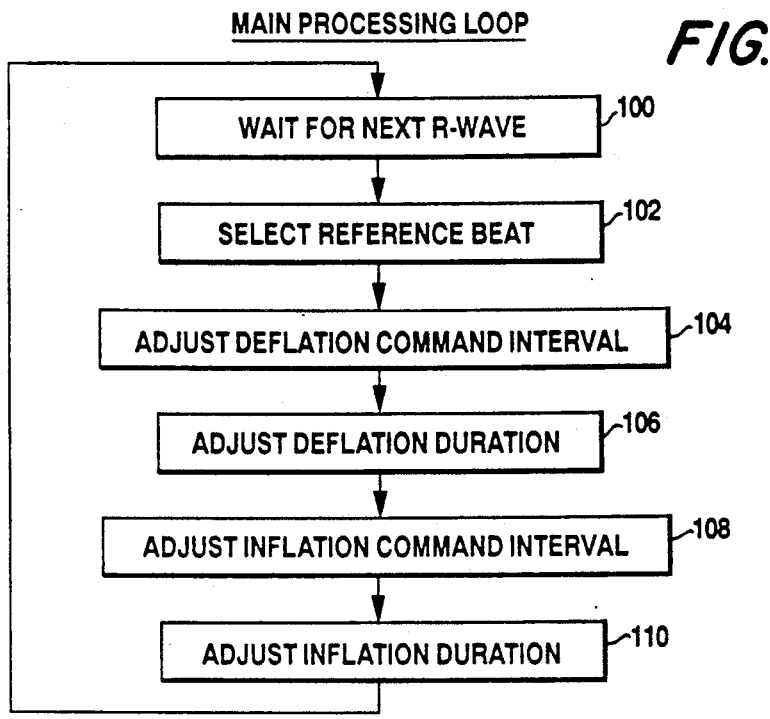
FIG. 7 is a flowchart ilustrating the steps of the main processing loop of the system and method of the present invention.

FIG. 7 illustrates in flowchart form the steps of the main processing loop of the control means. As embodied herein, and by way of example and not limitation, the reference heart beat may be selected by comparing the time interval between successive QRS waves of the latest heart beat, and the aortic pressure measured at the peak of the heart systole for the latest heart beat, with each of a predetermined number of preceding heart beats. A match is found if the time interval between successive QRS waves and the aortic pressure at peak systole for any one of the preceding number of heart beats are within 12.5% of those values for the latest heart beat. If no match is found these criteria may be successively eased to higher percentage values to find a match. If no match is found with the predetermined number of preceding heart beats, a default rule is entered into within the control means and the physiologic events and assist system parameters of the immediately preceding heart beat are used as the base line for adjusting those values for the present heart beat.

With reference to FIG. 7, at step 100 the control means awaits the next occurrence of the QRS wave. At step 102 a reference heart beat is selected from a predetermined number of preceding heart beats, which by way of example may be 32 heart beats. At step 104 the time delay for initiation of deflation of the pumping bladder is adjusted. At step 106 the time duration of deflation of the pumping bladder is adjusted. At step 108 the time delay for initiation of inflation is adjusted. And, at step 110 the duration of inflation of the pumping bladder is adjusted. Each of adjusting steps 104, 106, 108 and 110 will be discussed in detail below.

Figure 6:
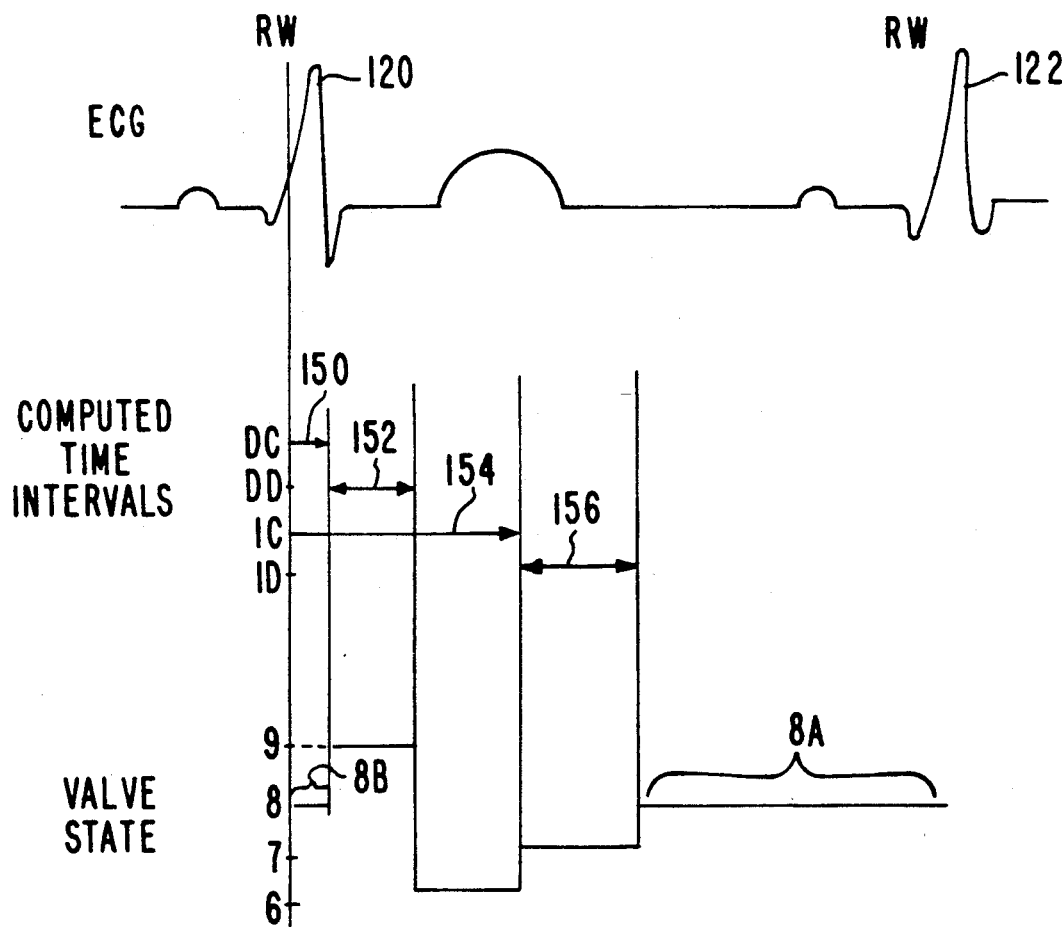
FIG. 6 illustrates on a time line the temporal relationship of the initiation of inflation and initiation of deflation of the pumping bladder and the durations of inflation and deflation of the pumping bladder during one heart cycle relative to the respective valve states illustrated in FIG. 3.

Control of gas handling subsystem 34 by processor 30 to accomplish the essential synchronization of the inflation/deflation cycle of pumping bladder 12 to the closing and opening of the patient's aortic valve is implemented totally automatically by the processor 30 based on the physiologic events detected from the electrocardiogram, the aortic pressure, and the drive line pressure in conduit 56. The relationship of these events and the temporal rules for synchronization are illustrated in FIG. 6 and the flowcharts shown in FIGS. 8-11, wherein the following abbreviations are used:

DN = dicrotic notch (closing of the aortic valve);
ED = end diastole (opening of the aortic valve);
IB = beginning of pumping bladder inflation;
PA = peak diastolic assistance;
PS = peak heart systole;
RW = occurrence of a QRS wave as determined from the electrocardiogram;
RW-INT = time interval between successive QRS waves;

Any of the above abbreviations followed by AP corresponds to aortic pressure measured at the respective event;

Any of the above abbreviations followed by DLY corresponds to the delay time elapsed from occurrence of the respective QRS wave to the respective event;

Any of the above abbreviations followed by DP corresponds to the drive pressure in conduit 56 measured at the respective event;

CB = current heart beat; and
RB = reference heart beat.

Processor 30 adjusts or selects four independent time intervals: deflation command time interval (DC), i.e., the time that the system should wait after detection of the QRS wave for the present heart beat before initiating deflation of pumping bladder 12; deflation duration time interval (DD), i.e., the length of time that the gas handling subsystem is actively removing shuttle gas from pumping bladder 12; the inflation command time interval (IC), i.e., the time that the system waits after detection of the QRS wave for the present heart beat before initiating inflation of the pumping bladder; and inflation duration (ID), i.e., the length of time that the gas handling subsystem is actively adding shuttle gas to pumping bladder 12.

The respective open and closed positions of valves 48, 50, 58, 60, 62 and 66 of the gas handling subsystem, as designated and controlled by processor 30 for each of the events DC, DD, IC, and ID, are reflected in FIGS. 3 and 6 with reference to valve states 6-9. However, there is not necessarily a one to one correspondence between the respective events and the valve states 6-9 since the various delay times precipitating each event are not necessarily timed from a common occurrence or starting point as can be seen in FIG. 6.

The transition from state 6 to state 7 represents initiation of inflation of the pumping bladder 12, which time of initiation of inflation corresponds to the time interval IC. In state 7, control valve 48 is open to connect source of compressed air 44 to air side 35 of isolation chamber 36 thereby expanding diaphragm 38. Common valve 58 is opened and the pressurized helium residing in the helium side of isolation chamber 37 inflates pumping bladder 12.

Figure 5:
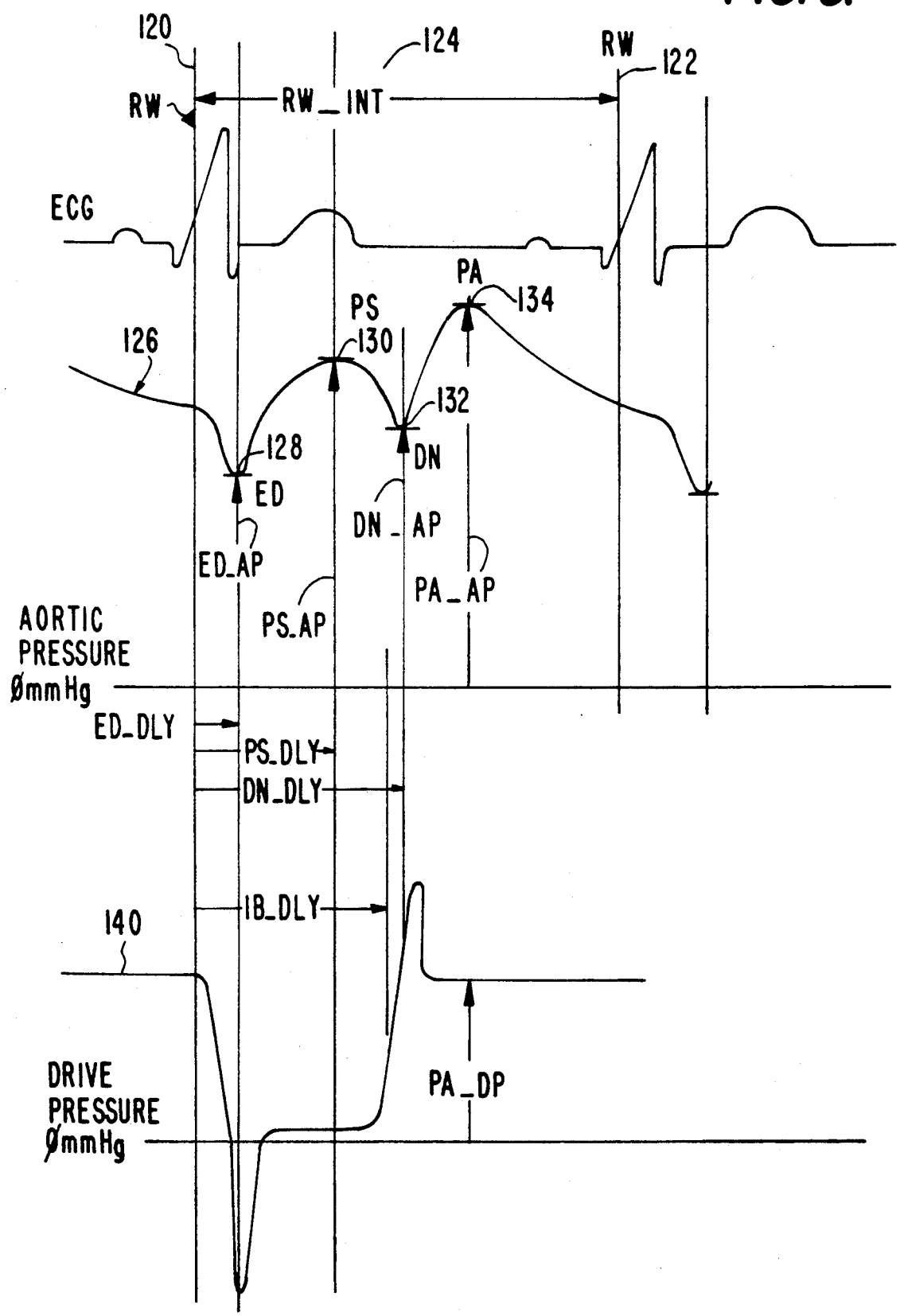
FIG. 5 illustrates on a time line the occurrences of selected physiologic events and related pneumatic events detected by the sensing means of the system incorporating the teachings of the present invention.

For each current heart beat, processor 30 adjusts the time period from detection of the QRS wave for the current heart beat until initiation of the inflation command in accordance with detected physiologic events and a predetermined set of rules. As embodied herein, the detected physiologic events are determined from the monitored electrocardiogram and the monitored aortic pressure as sensed by electrodes 18 and pressure sensor 20, respectively. With reference to FIG. 5 there is shown a typical readout of the electrocardiogram (ECG), aortic pressure (AP), and drive line pressure (DP) in conduit 56 for one heart beat represented by successive QRS waves on the electrocardiogram. The ECG readout is shown at the top of FIG. 5 where successive QRS waves 120 and 122 are illustrated with the time interval 124 between QRS waves 120 and 122 being further indicated. Immediately below the ECG in FIG. 5 is a graphical representation 126 of the aortic pressure as monitored by pressure sensor 20. Point 128 of graph 126 represents end diastole (ED), i.e., opening of the aortic valve. Point 130 represents peak heart systole (PS). Point 132 represents the dicrotic notch (DN), i.e., closing of the aortic valve. Point 134 represents peak diastolic assistance (PA).

Immediately below graph line 126 in FIG. 5 there is shown a graphical representation 140 indicative of the drive line pressure of the helium in conduit 56 of the gas handling subsystem during the interval 124. Graph line 140 also illustrates the pressure in conduit line 56 at the time of initiation of the inflation command of pumping bladder 12 and the drive line pressure in conduit 56 when pumping bladder 12 is inflated.

INFLATION INITIATION COMMAND SUB-ROUTINE

With continued reference to FIG. 5 and concurrent reference to FIG. 10, there is illustrated by way of example and not limitation, a flowchart presenting the rules utilized by processor 30 to adjust the inflation command time interval for the current heart beat (IC(CB)). Initially, processor 30 selects a reference heart beat utilizing the selection criteria previously described. At step 200, processor 30 sets the inflation command time interval for the current heart beat (IC(CB)) equal to that of the selected reference heart beat (IC(RB)). At step 202 processor 30 determines whether the delay time from the QRS wave of the reference heart beat to beginning of pumping bladder inflation (IB_DLY(RB)) is greater than the time delay from the QRS wave to the occurrence of the dicrotic notch in the reference heart beat (DN_DLY(RB)) plus four milliseconds. If this relationship holds true then the inflation command time inteval is decremented by four ms. Otherwise, the inflation command time interval for the current heart beat is incremented by four milliseconds.

At step 204 processor 30 determines whether the delay time from the QRS wave of the reference heart beat to the beginning of pumping bladder inflation on the reference heart beat is greater than the delay time from the QRS wave of the reference heart beat to the occurrence of the dicrotic notch of the reference heart beat plus 32 milliseconds. If this relationship holds true, then the delay time from the QRS wave to the inflation command on the current heart beat is reset to the delay time from the QRS wave of the reference heart beat to the inflation command on the reference heart beat minus eight milliseconds.

At step 206 processor 30 determines whether the delay time from the QRS wave to the beginning of pumping bladder inflation on the reference heart beat is less than the delay time from the QRS wave to the dicrotic notch on the reference heart beat minus 20 milliseconds. If this relationship holds true, then the inflation command on the current heart beat is reset to the inflation command time interval of the reference heart beat plus eight milliseconds.

At step 208 processor 30 determines whether the aortic pressure at the occurrence of the dicrotic notch 132 on the reference heart beat (DN_AP(RB)) is greater than the aortic pressure at peak heart systole 130 on the reference heart beat (PS_AP(RB)) minus five mm Hg. If this relationship holds true, then the inflation command time interval on the current heart beat is reset to the inflation command time interval from the reference heart beat plus 12 milliseconds.

At step 210 processor 30 determines whether the beginning of pumping bladder inflation on the reference heart beat has been located, and if not, the inflation command delay time for the current heart beat is reset to the time interval between occurrence of the QRS wave on the reference heart beat and the occurrence of the dicrotic notch on the reference heart beat.

At step 212 processor 30 determines whether the inflation command time interval on the current heart beat (IC(CB)) is less than 100 milliseconds and if so, resets the inflation command time interval for the current heart beat (IC(CB)) to 100 milliseconds.

At step 214 processor 30 determines whether the inflation command time interval for the current heart beat (IC(CB)) is greater than 500 milliseconds and if so, resets the inflation time interval command on the current heart beat to 500 milliseconds.

Utilizing the predetermined rules and assist system parameters illustrated in FIG. 10 in steps 200-214, processor 30 selects or adjusts a time of initiation of inflation of pumping bladder 12 from the occurrence of the QRS wave for each current heart beat. This process or set of rules and decision making is repeated for each heart beat. The hierarchy of the rules illustrated in steps 200-214 proceed as illustrated from top to bottom in FIG. 10.

Furthermore, the absolute values for incrementing, decrementing or setting the time of initiation of inflation of pumping bladder 12 as illustrated in FIG. 10 are not limiting of the scope of the present invention. These absolute values of the amounts of adjustment of the inflation command time interval may be modified to better assist the control means in converging on an optimal set of values for inflating and deflating pumping bladder 12 thereby increasing the effect of assistance on the patient. The values presented herein for adjustment of the inflation command time interval are by way of example and not limitation.

Moreover, it is emphasized that the present invention is not limited to the specific sequence or commands illustrated and described with respect to steps 200-214, this being but one present preferred embodiment of the Inflation Initiation Subroutine. Those skilled in the art might add or delete steps of this sub-routine to "fine tune" the present invention to a specific desired result for the assistance provided a patient while remaining within the scope of the present invention. The possibilities of such "fine tuning" are unlimited and therefore not described herein. Similarly, the remaining three subroutines described herein below, i.e., the Inflation Duration Sub-routine, the Deflation Initiation Sub-routine, and the Deflation Duration Sub-routine, represent but one presently preferred embodiment for implementing the present invention with permutations or different combinations of steps being possible for each while remaining within the scope of the present invention.

INFLATION DURATION SUB-ROUTINE

With continued reference to FIG. 5 and concurrent reference to FIG. 11, there is illustrated by way of example and not limitation, a flowchart disclosing one embodiment of the rules for determining and adjusting the duration of inflation of pumping bladder 12.

At step 300 the duration of inflation of pumping bladder 12 for the current heart beat is initially set equal to the duration of inflation of pumping bladder 12 on the reference heart beat. At step 302 processor 30 determines whether the drive pressure in conduit 56 at peak diastolic assistance 134 (PA_DP(RB)) on the reference heart beat is greater than the aortic pressure at peak diastolic assistance (PA_AP(RB)) on the reference heart beat plus 10 mm Hg. If this relationship holds true, then the duration of inflation of pumping bladder 12 on the current heart beat is set equal to the duration of inflation of pumping bladder 12 on the reference heart beat minus four milliseconds. Otherwise, the duration of inflation of pumping bladder 12 on the current heart beat is set equal to the duration of inflation of pumping bladder 12 on the reference heart beat plus four milliseconds.

At step 304 processor 30 determines whether the time period or delay from occurrence of the QRS wave on the reference heart beat to peak diastolic assistance on the reference heart beat (PA_DLY(RB)) has been located. If not, then the duration of inflation of pumping bladder 12 on the current heart beat is reset to the duration of inflation of pumping bladder 12 on the reference heart beat minus four milliseconds.

At step 306 processor 30 determines whether the duration of inflation of pumping bladder 12 on the current heart beat is less than 40 milliseconds and if so, resets the duration of inflation of pumping bladder 12 on the current heart beat equal to 40 milliseconds.

Finally, processor 30 determines whether the duration of inflation of pumping bladder 12 for the current heart beat has been set with a value greater than 200 milliseconds, and if so, resets the duration of inflation of pumping bladder 12 for the current heart beat equal to 40 milliseconds. In the manner described above with reference to FIG. 11, processor 30 adjusts the duration of inflation of pumping bladder 12 for each successive heart beat.

Here again, the absolute values and steps disclosed for incrementing, decrementing or setting the time period for duration of inflation of pumping bladder 12 as illustrated in FIG. 11 and described above are presented by way of example and not limitation of the scope of the present invention.

DEFLATION INITIATION SUB-ROUTINE

Figure 8:
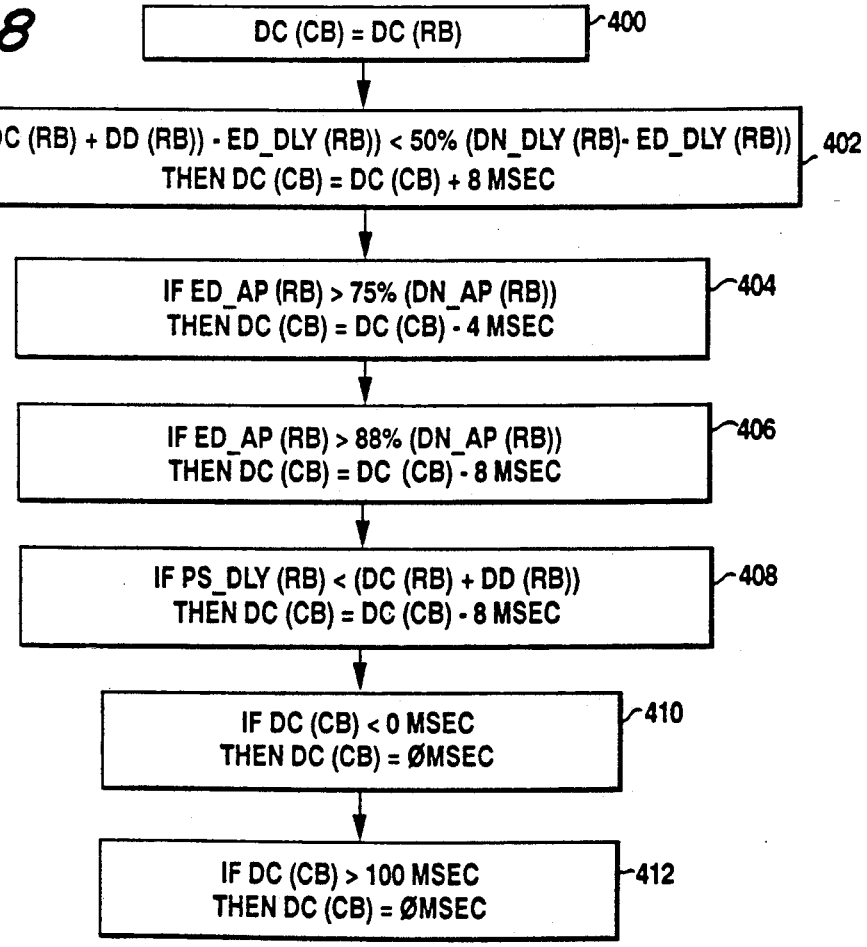
FIG. 8 is a flowchart illustrating the steps or rules for the Deflation Command Adjustment Sub-routine of the main processing loop.

The rules by which processor 30 sets the time delay from occurrence of the QRS wave of the current heart beat to initiation of the deflation of pumping bladder 12 in the present embodiment are illustrated in the flowchart of FIG. 8. At step 400 the time interval between occurrence of the QRS wave and initiation of deflation of pumping bladder 12 on the current heart beat (DC(CB)) is set equal to the time interval from occurrence of the QRS wave on the reference heart beat to initiation of deflation of pumping bladder 12 on the reference heart beat (DC(RB)).

At step 402 processor 30 determines whether the sum of the time intervals on the reference heart beat for initiation of deflation (DC(RB)) and duration of deflation (DD(RB)) of pumping bladder 12 minus the time delay between occurrence of the QRS wave and end of diastole on the reference heart beat (ED_DLY(RB)) is less than 50% of the difference between the time delay between occurrence of the QRS wave and occurrence of the dicrotic notch on the reference heart beat (DN_DLY(RB)) minus the time delay between occurrence of the QRS wave and the end of diastole on the reference heart beat (ED_DLY(RB)). If this relationship holds true, processor 30 increases the deflation command time interval for the current heart beat by eight milliseconds.

At step 404 processor 30 determines whether aortic pressure at end of diastole on the reference heart beat (ED_AP(RB)) is greater than 75% of aortic pressure at occurrence of the dicrotic notch on the reference heart beat (DN_AP(RB)). If so, then the deflation command time interval is decremented by four milliseconds.

At step 406 processor 30 determines whether aortic pressure at the end of diastole on the reference heart beat is greater than 88% of the aortic pressure at occurrence of the dicrotic notch on the reference heart beat and if so, decrements the deflation command time interval for the current heart beat by eight milliseconds.

At step 408 processor 30 determines whether the time interval between occurrence of the QRS wave on the reference heart beat and the peak heart systole on the reference heart beat (PS_DLY(RB)) is less than the sum of the deflation command time interval on the reference heart beat plus the deflation duration time interval on the reference heart beat. If so, processor 30 decrements the deflation command time interval for the current heart beat by eight milliseconds.

At step 410 processor 30 determines whether the deflation command time interval for the current heart beat is less than zero milliseconds and if so, resets the deflation command time interval for the current heart beat equal to zero milliseconds.

At step 412 processor 30 determines whether the deflation command time interval for the current heart beat is greater than 100 milliseconds and if so, resets the deflation command time interval for the current heart beat equal to zero milliseconds.

Here again, the absolute values and steps disclosed for decrementing, incrementing, or setting the time of initiation of deflation of pumping bladder 12 are presented by way of example and are not limiting of the scope of the present invention.

DEFLATION DURATION SUB-ROUTINE

With continued reference to FIG. 5, and concurrent reference to FIG. 9, there is illustrated a flowchart disclosing the presently preferred embodiment of the rules for determining and adjusting the duration of deflation of pumping bladder 12.

Initially, processor 30 sets the duration of deflation for the current heart beat equal to the duration of deflation for the selected reference heart beat at step 500.

At step 502 processor 30 determines whether the drive line pressure in conduit 56 of the gas handling subsystem upon initiation of inflation of pumping bladder 12 (IC_DP(RB)) during the reference heart beat was greater than 10 mm Hg. If so, processor 30 increments the duration of deflation of pumping bladder 12 during the current heart beat by four milliseconds. If not, processor 30 decrements the duration of deflation of pumping bladder 12 for the current heart beat by four milliseconds.

At step 504 processor 30 determines whether the duration of deflation of pumping bladder 12 during the current heart beat is set less than 40 milliseconds and if so, resets the duration of deflation of pumping bladder 12 during the current heart beat to 40 milliseconds.

At step 506 processor 30 determines whether the duration of deflation of pumping bladder 12 during the current heart beat is set to be greater than 200 milliseconds, and if so, resets the duration of deflation of the current heart beat at 200 milliseconds.

Here again, the absolute values and steps by which the duration of deflation is incremented, decremented, or set are presented by way of example and are not limiting of the scope of the present invention.

The sequence through which processor 30 executes each of the four sub-routines described above is illustrated in FIGS. 6 and 7. In the preferred embodiment each of the time intervals corresponding to events DC, DD, IC, and ID are set or selected at the detection of the respective QRS wave by processor 30. However, the actual operations performed by processor 30 in carrying out the sub-routines described above may be considered to occur sequentially for purposes of clarity. Between successive QRS waves 120 and 122 the deflation command (DC) time interval is selected, i.e., adjusted, and deflation of pumping bladder 12 is initiated at that time delay after occurrence of QRS wave 120 as represented by single headed arrow 150. The deflation duration time interval (DD) is also selected, i.e., adjusted, and the pumping bladder 12 is deflated for that time interval as represented by double headed arrow 152. The inflation command time interval (IC) is selected, i.e., adjusted, and inflation of pumping bladder 12 is initiated at that time interval after occurrence of QRS wave 120 as represented by single headed arrow 154. Finally, the inflation duration (ID) is selected, i.e., adjusted, and pumping bladder 12 is inflated for that time interval as represented by double headed arrow 156. Each of these four time intervals are recomputed or adjusted for each heart beat. Valves 48, 50, 58, 60, 62 and 66 of the gas handling subsystem are cycled through states 6, 7, 8 and 9 as illustrated in FIG. 3.

This sequencing of the valves of the gas handling subsystem through states 6-9 is also illustrated in FIG. 12 which presents a flowchart illustrating the sequencing of the valves through the various states. Therein, valve state 8 is divided into two substates 8A and 8B. State 8A corresponds to the time duration between the end of the period of duration of inflation of pumping bladder 12 and the occurrence of the next QRS wave. State 8B corresponds to the time from occurrence of the QRS wave to initiation of deflation, i.e., issuance of the deflation command (DC), of pumping bladder 12.

Assist system parameters are selected, i.e., adjusted, for each current heart beat (CB) using the algorythms and assist system parameters described above. The physiologic events and prior values of assist system parameters used are those of a reference heart beat RB which may be chosen from a predetermined number of prior heart beats. The present invention thus provides a fully automatic method and system for assisting the circulation of blood in a patient without the necessity of operator involvement and while automatically optimizing the effects of assistance on the patient.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. An in-series left ventricular assist system for assisting the circulation of blood in a patient, comprising:
   a pumping bladder for disposal in the thoracic aorta of the patient;
   means for detecting selected physiologic events relating to each heart beat;
   gas handling means for inflating and deflating said pumping bladder in accordance with said detected physiologic events and a predetermined set of assist system parameters, said gas handling means including a shuttle gas circuit having a shuttle gas therein, means for pressurizing and depressurizing said shuttle gas in said circuit, means for adding and exhausting shuttle gas to and from said shuttle gas circuit, and valve means for regulating the flow of shuttle gas to and from said pumping bladder; and control means for evaluating the effects on blood circulation of inflation and deflation of said pumping bladder and the corresponding assistance on the patient for each heart bear, and for automatically adjusting said assist system parameters for each subsequent heart beat to optimize effects of assistance of said pumping bladder on the patient; wherein said valve means is operable to an open position for a predetermined period of time to inflate said pumping bladder, and said control means is operable to selectively adjust said predetermined period of time said valve means is open to inflate each heart beat such that the amount of shuttle gas admitted into said pumping bladder is sufficient for complete inflation, independent of the volume of the pumping bladder, while maintaining a transmembrane pressure of less than 50 mm Hg.

2. The in-series left ventricular assist system of claim 1, wherein said detecting means includes means for sensing said selected physiologic events, said sensing means being disposed proximate said pumping bladder.

3. The in-series left ventricular assist system of claim 2, wherein said sensing means includes means for sensing the electrocardiogram and the aortic blood pressure of the patient, and for generating signals in accordance with said sensed electrocardiogram and aortic blood pressure.

4. The in-series left ventricular assist system of claim 1, wherein said gas handling means includes means for selectively adjusting for each heart beat, the amount of gas used to inflate said pumping bladder.

5. The in-series left ventricular assist system of claim 1, including:
an isolation chamber connected on one side thereof to said shuttle gas circuit;
an air circuit connected to the opposite side of said isolation chamber; and
wherein said pressurizing means includes a source of compressed air and a regulated vacuum, and control valve means for connecting said source of compressed air and said regulated vacuum to said air circuit.

6. The in-series left ventricular assist system of claim 5, wherein said isolation chamber includes a diaphragm dividing said isolation chamber into an air side and a shuttle gas side, and means for detecting displacement of said diaphragm in said isolation chamber.

7. The in-series left ventricular assist system of claim 1, wherein said detecting means includes means for detecting each occurrence of QRS wave and said control means includes means for measuring the time interval between successive QRS waves, and said detecting means further includes pressure sensing means for determining the aortic pressure of the patient, said detecting means and said control means begin operable, in combination, to determine, for each heart beat,
a) a time interval between detection of the QRS wave and opening of the aortic valve;
b) aortic pressure at opening of the aortic valve;
c) a time interval between detection of the QRS wave and closing of the aortic valve;
d) aortic pressure at closing of the aortic valve;
e) a time interval between detection of the QRS wave and an initial effect on aortic pressure caused be inflation of said pumping bladder; and
f) respective time intervals between detection of the QRS wave and the end of inflation and the end of deflation of said pumping bladder.

8. The in-series left ventricular assist system of claim 7, including means for storing said detected physiologic events and associated assist system parameters for a predetermined number of preceding heart beats prior to each subsequent heart beat, and means for comparing said detected physiologic events of each heart beat with said stored physiologic events to select at least one of said predetermined number of preceding heart beats as a reference heart beat, and wherein said control means includes an inflation means for initiating inflation of said pumping bladder at a predetermined time delay after detection of the QRS wave for each heart beat, said predetermined time delay being selected by said inflation means in accordance with said time interval between detection of the QRS wave and initial effect on aortic pressure for said reference heart beat.

9. The in-series left ventricular assist system of claim 8, wherein said control means includes means for re-computing said time delay from the detected QRS to the inflation of said pumping bladder for each heart beat according to the following rules:
a) if on said reference heart beat the detected beginning of balloon inflation occurred before the detection of the closing of the aortic valve, then increase said time delay for the present heart beat by a predetermined amount in excess of said time delay on said reference heart beat;
b) if on said reference heart beat the detected beginning of balloon inflation occurred after the detection of the closing of the aortic valve, then decrease said time delay for the present heart beat by a predetermined amount from said time delay on said reference heart beat.

10. The in-series left ventricular assist system of claim 7, wherein said control means includes means for initiating deflation of said pumping bladder at a predetermined time delay after detection of the QRS wave, said predetermined time delay for initiating deflation being selected by said deflation means in accordance with:
a) the temporal relationship between said detected opening of the aortic valve, end of pumping bladder deflation, and detected closing of the aortic valve; and
b) the aortic pressure at the opening of the aortic valve and the aortic pressure at the closing of the aortic valve.

11. An in-series left ventricular assist system for assisting the circulation of blood in a patient, comprising:
a pumping bladder for disposal in the thoracic aorta of the patient;
means for detecting selected physiologic events relating to each heart beat;
gas handling means for inflating and deflating said pumping bladder in accordance with said detecting physiologic events and a predetermined set of assist system parameters, said gas handling means including a shuttle gas circuit having a shuttle gas therein, means for pressurizing and depressurizing said shuttle gas in said circuit, means for adding and exhausting shuttle gas to and from said shuttle gas circuit, and valve means for regulating the flow of shuttle gas to and from said pumping bladder; and shuttle gas volume control means for maintaining a selected volume of shuttle gas in said shuttle gas circuit, said shuttle gas volume control means including means for monitoring a difference between pumping bladder pressure and the patient's aortic pressure when said pumping bladder is inflated, said shuttle gas volume control means being operable to control said means for adding and exhausting shuttle gas in accordance with said monitored difference between pumping bladder pressure and aortic pressure.

12. An in-series left ventricular assist system for assisting the circulation of blood in a patient, comprising:
a pumping bladder for disposal in the thoracic aorta of the patient;
means for detecting selected physiologic events relating to each heart beat;
gas handling means for inflating and deflating said pumping bladder in accordance with said detected physiologic events and a predetermined set of assist system parameters, said gas handling means including a shuttle gas circuit having a shuttle gas therein, means for pressurizing and depressurizing said shuttle gas in said circuit, means for adding and exhausting shuttle gas to and from said shuttle gas circuit, and valve means for regulating the flow of shuttle gas to and from said pumping bladder;
control means for evaluating the effects on blood circulation of inflation and deflation of said pumping bladder and the corresponding assistance on the patient for each heart beat, and for automatically adjusting said assist system parameters for each subsequent heart beat to optimize effects of assistance of said pumping bladder on the patient;
wherein said valve means is operable to an open position for a predetermined period of time to deflate said pumping bladder, and said control means is operable to selectively adjust said predetermined period of time said valve means is open to deflate said pumping bladder for each heart beat such that the amount of shuttle gas removed from said pumping bladder is sufficient to completely empty said balloon while limiting residual intraballoon pressure to no less than 0 mm Hg.

13. An in-series left ventricular assist system for assisting the circulation of blood in a patient, comprising:
a pumping bladder for disposal in the thoracic aorta of the patient;
means for detecting selected physiologic events relating to each heart beat;
gas handling means for inflating and deflating said pumping bladder in accordance with said detected physiologic parameters and a predetermined set of assist system parameters;
means for storing said detected physiologic events and associated assist system parameters for a predetermined number of preceding heart beats prior to each subsequent heart beat;
means for comparing the detected physiologic events of each heart beat with said stored physiologic events to select at least one of said predetermined number of preceding heart beats as a reference heart beat; and
control means for evaluating the effects of inflation and deflation of said pumping bladder and the corresponding assistance on the patient for said selected preceding reference heart beat, and for altering said assist system parameters for each subsequent heart beat in accordance with said evaluated effects of assistance of said pumping bladder on the patient for said selected preceding reference heart beat.

14. The in-series left ventricular assist system of claim 13, wherein said detecting means includes for detecting each occurrence of a QRS wave and pressure sensing means for detecting the aortic pressure of the patient, and said control means includes means for measuring the time interval between successive QRS waves, said detecting means and said control means being operable, in combination, to determine for each heart beat:
 a) a time interval between detection of the QRS wave and opening of the aortic valve;
 b) aortic pressure at opening of the aortic valve;
 c) a time interval between detection of the QRS wave and closing of the aortic valve;
 d) aortic pressure at closing of the aortic valve;
 e) a time interval between detection of the QRS wave and an initial effect on aortic pressure caused be inflation of said pumping bladder; and
 f) respective time intervals between detection of the QRS wave and the end of inflation and the end of deflation of said pumping bladder.

15. The in-series left ventricular assist system of claim 14, wherein said control means includes an inflation means for initiating inflation of said pumping bladder at a predetermined time delay after detection of the QRS wave for each subsequent heart beat, said predetermined time delay being selected by said inflation means in accordance with said time interval between detection of the QRS wave and initial effect on aortic pressure for said selected preceding heart beat.

16. The in-series left ventricular assist system of claim 15, wherein said control means includes means for recomputing said time delay from the detected QRS wave to the initiation of inflation of said pumping bladder for each subsequent heart beat according to the following rules:
 a) if on said selected preceding heart beat the detected beginning of balloon inflation occurred before the detection of the closing of the aortic valve, then increase said time delay for the present heart beat by a predetermined amount in excess of said time delay on said reference heart beat;
 b) if on said selected preceding heart beat the detected beginning of balloon inflation occurred after the detection of the closing of the aortic valve, then decrease said time delay for the present heart beat by a predetermined amount from said time delay on said reference heart beat.

17. The in-series left ventricular assist system of claim 14, wherein said control means includes means for initiating deflation of said pumping bladder a predetermined time delay after detection of the QRS wave, said predetermined time delay for initiating deflation being selected by said control means in accordance with:
 a) the temporal relationship between said detected opening of the aortic valve, end of pumping bladder deflation, and detected closing of the aortic valve; and
 b) the aortic pressure at the opening of the ortic valve and the aortic pressure at the closing of the aortic valve.

18. A method for controlling inflation and deflation timing of an in-series left ventricular assist system, comprising the steps of:
detecting selected physiologic events relating to each heart beat;

inflating and deflating said pumping bladder at selected times;

storing, for a selected number of previous heart beats, the detected physiologic events relating to said previous heart beats and said selected times of inflation and deflation of said pumping bladder during said previous heart beats;

comparing said detected physiologic events of each subsequent heart beat with said stored physiologic events of said previous heart beats;

selecting at least one of said previous heart beats in accordance with said comparison of physiologic events; and adjusting the inflation and deflation timing of said pumping bladder for each subsequent heart beat in accordance with the effects of inflation and deflation of said pumping bladder on said selected previous heart beat.

19. A method of controlling, for each heart beat of a patient, the volume of inflation of an in-series left ventricular assist device, the assist device including a drive unit and pump means for cyclically inflating and deflating a pumping bladder disposed in the thoracic aorta of the patient, comprising the steps of:

detecting selected physiologic events relating to each heart beat;

detecting selected pneumatic events relating to each pump cycle within the drive unit;

pumping shuttle gas into said pumping bladder for a selected time interval;

storing, for a selected number of preceding heart beats, the detected physiologic events, the detected pneumatic events, and the associated inflation time interval; decrementing the inflation time interval where driveline pressure exceeds aortic pressure by more than a nominal 10 mm Hg, measured at the peak of diastole; and incrementing the inflation time interval when driveline pressure does not exceed aortic pressure by more than a nominal 10 mm Hg, measured at the peak of diastolee.

20. A method of controlling, for each heart beat of a patient, the volume of deflation of an in-series left ventricular assist device, the assist device including pump means and associated drive unit for cyclically inflating and deflating a pumping bladder disposed in the thoracic aorta of the patient, comprising the steps of:

detecting selected physiologic events relating to each heart beat;

detecting selected pneumatic events relating to each pump cycle within the drive unit;

pumping shuttle gas out of said pumping bladder for a selected time interval;

storing, for a selected number of preceding heart beats, the detected physiologic events, the detected pneumatic events, and the associated deflation time interval;

incrementing the deflation time interval where driveline pressure exceeds a nominal 10 mm Hg, measured just prior to the issuance of an inflation command; and decrementing the deflation time interval where the driveline pressure does not exceed a nominal 10 mm Hg, measured just prior to the issuance of an inflation command.

21. A method for adjusting the inflation timing of a pumping bladder of an in-series left ventricular assist system, comprising the steps of:

detecting selected physiologic events relating to each heart beat;

inflating said pumping bladder at a predetermined time delay after detection of at least one of the selected physiologic events;

determining the effects of pumping bladder inflation on the patient for each heart beat;

calculating a revised time delay for inflation of the pumping bladder on the next heart beat based on the effects of pumping bladder inflation on the patient for at least one of the preceding heart beats; and adjusting the predetermined time delay for inflation of the pumping bladder on subsequent heart beats by increments which are a fraction of the difference between the predetermined time delay and the revised time delay.

* * * * *

UNITED STATES PATENT AND TRADEMARK OFFICE
CERTIFICATE OF CORRECTION

PATENT NO. : 5,169,379
DATED : December 8, 1992
INVENTOR(S) : Paul S. Freed et al.

It is certified that error appears in the above-identified patent and that said Letters Patent is hereby corrected as shown below:

Claim 1, column 19, line 9, change "bear" to --beat--.

Claim 7, column 19, line 61, change "begin" to --being--.

Claim 14, column 22, line 5, after "includes" insert --means--.

In the Abstract, line 3, change "thoractic" to --thoracic--.

Signed and Sealed this

Twelfth Day of October, 1993

Attest:

BRUCE LEHMAN

Attesting Officer    Commissioner of Patents and Trademarks